(12) United States Patent
Rack et al.

(10) Patent No.: US 8,629,279 B2
(45) Date of Patent: Jan. 14, 2014

(54) PROCESS FOR MANUFACTURING 5-FORMYL-PYRIDINE-2,3-DICARBOXYLIC ACID ESTERS

(75) Inventors: Michael Rack, Eppelheim (DE); Joachim Gebhardt, Wachenheim (DE); Frederik Menges, Schriesheim (DE); Michael Keil, Freinsheim (DE); Rodney F. Klima, Quincy, IL (US); David Cortes, Quincy, IL (US); Robert Leicht, Hannibal, MO (US); Helmut Zech, Bad Duerkheim (DE); Jochen Schröder, Lambsheim (DE)

(73) Assignee: BASF SE, Ludwigshafen (DE)

( * ) Notice: Subject to any disclaimer, the term of this patent is extended or adjusted under 35 U.S.C. 154(b) by 221 days.

(21) Appl. No.: 13/133,013

(22) PCT Filed: Dec. 7, 2009

(86) PCT No.: PCT/EP2009/066495
§ 371 (c)(1),
(2), (4) Date: Jun. 6, 2011

(87) PCT Pub. No.: WO2010/066668
PCT Pub. Date: Jun. 17, 2010

(65) Prior Publication Data
US 2011/0245505 A1 Oct. 6, 2011

Related U.S. Application Data

(60) Provisional application No. 61/120,957, filed on Dec. 9, 2008.

(51) Int. Cl.
*C07D 213/48* (2006.01)
*C07D 213/55* (2006.01)
(52) U.S. Cl.
USPC .................. 546/321; 546/116; 546/272.7
(58) Field of Classification Search
USPC ...................... 546/116, 321, 272.7
See application file for complete search history.

(56) References Cited

U.S. PATENT DOCUMENTS

| 5,026,859 | A | 6/1991 | Finn |
| 5,334,576 | A | 8/1994 | Doehner, Jr. et al. |
| 5,378,843 | A | 1/1995 | Strong |
| 5,760,239 | A | 6/1998 | Wu |

FOREIGN PATENT DOCUMENTS

| DE | 3330604 | 3/1985 |
| EP | 0 144 595 | 6/1985 |
| EP | 0 184 027 | 6/1986 |
| EP | 0 322 616 | 7/1989 |
| EP | 0 539 676 | 5/1993 |
| EP | 0 548 532 | 6/1993 |
| EP | 0 747 360 | 12/1996 |
| EP | 0 933 362 | 8/1999 |

(Continued)

OTHER PUBLICATIONS

Zubrik, James. W., "The Organic Chem Lab Survival Guide", copyright 1984, 1988, by John Wiley & Sons, Inc.

(Continued)

*Primary Examiner* — David K O Dell
(74) *Attorney, Agent, or Firm* — Brinks Gilson & Lione

(57) ABSTRACT

A process for manufacturing a 5-formyl-pyridine-2,3-dicarboxylic acid ester (I) wherein Z is hydrogen or halogen; $Z^1$ is hydrogen, halogen, cyano or nitro and $R^1$, $R^2$ are independently $C_1$-$C_{10}$-alkyl, comprising the steps of (i) reacting a compound of formula (II), wherein the symbols are as in formula (I), with a nitrosation agent (III) $R^3$—O—N=O (III) wherein $R^3$ is $C_1$-$C_8$-alkyl, in the presence of an alkali metal or alkaline earth metal alcoholates or carbonates in a polar aprotic solvent at a temperature of from −45 to 40° C., to obtain an oxime compound (IV) where Z, $Z^1$, $R^1$ and $R^2$ are as in formula (I), and (ii) reacting oxime compound (IV) with an aliphatic $C_1$-$C_{10}$-aldehyde in the presence of a Lewis acid at a temperature in the range of from 0 to 100° C. The compounds of formula (I) are useful intermediates in the synthesis of herbicidal imidazolinones, like imazamox.

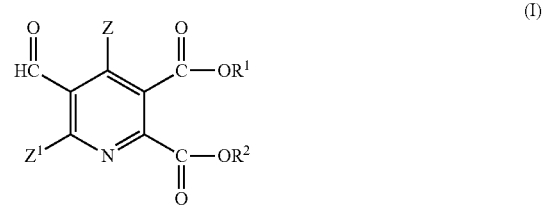

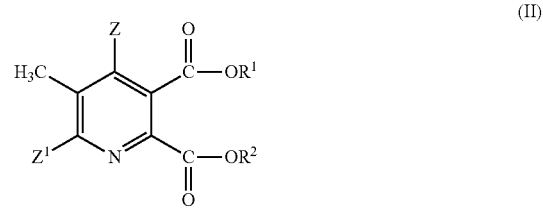

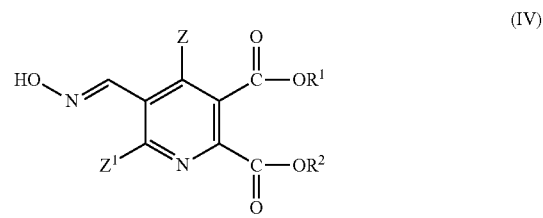

12 Claims, No Drawings

(56) References Cited

FOREIGN PATENT DOCUMENTS

| | | | | |
|---|---|---|---|---|
| JP | 62174069 A | * | 7/1987 | ........... C07D 401/04 |
| WO | WO 2010/054952 | | 5/2010 | |
| WO | WO 2010/055042 | | 5/2010 | |
| WO | WO 2010/055139 | | 5/2010 | |
| WO | WO 2010/057954 | | 5/2010 | |

OTHER PUBLICATIONS

Office Action dated Sep. 17, 2012, in U.S. Appl. No. 13/128,779, filed May 11, 2011.

International Search Report prepared in International Application No. PCT/EP2009/066495, filed Dec. 7, 2009.

International Preliminary Report on Patentability from corresponding International Application No. PCT/EP2009/066495, filed Dec. 7, 2009.

Bi, Q. et al., "Review on synthesis of imazamox", Modern Agrochemicals, (2007), pp. 10-14, vol. 6, No. 2.

Tagawa, Y. et al., "Reinvestigation of nitrosation of methlypyridines and their 1-oxides and deoxygenation of 3-pyridinecarbaldehyde 1-oxide oxime", Heterocycles, (1992), pp. 1605-1612, vol. 34, No. 8.

* cited by examiner

PROCESS FOR MANUFACTURING 5-FORMYL-PYRIDINE-2,3-DICARBOXYLIC ACID ESTERS

This application is a National Stage application of International Application No. PCT/EP2009/066495, filed Dec. 7, 2009, which claims the benefit of U.S. Provisional Application No. 61/120,957, filed Dec. 9, 2008, the entire contents of which are hereby incorporated herein by reference.

The invention relates to a process for manufacturing 5-formyl-pyridine-2,3-dicarboxylic acid esters, intermediates of this process and further conversion of these compounds to herbicidal 5-substituted-2-(2-imidazolin-2-yl) nicotinic acids, such as imazamox.

Derivatives of 2-(2-imidazolin-2-yl)nicotinic acids, like imazamox (2-[(RS)-4-isopropyl-4-methyl-5-oxo-2-imidazolin-2-yl]-5-methoxymethyl nicotinic acid),

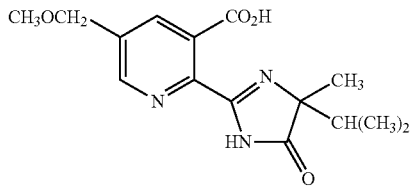

are useful selective herbicides which act as ALS-inhibitors and can be used in pre- and post-emergence applications.

Various processes for the synthesis of these compounds are known from the literature, see e.g. EP-A 0 322 616, EP-A 0 747 360, EP-A 0 933 362 or Q. Bi et al, Modern Agrochemicals 6(2)(2007) 10-14.

Although synthesis on an industrial scale is carried out by these methods there is still room for improvement, specifically in view of economical and ecological aspects, such as overall yield improvement or the avoidance of certain solvents or reagents.

EP-A 0 322 616 discloses the preparation of 5-chloromethyl-pyridine-2,3-dicarboxylic acid anhydrides by chlorination of respective 5-methyl compounds and further conversion of these compounds to herbicidal imidazolinones.

One task of the invention is to provide improved processes and new useful intermediates for the synthesis of 5-chloromethyl-pyridine-2,3-dicarboxylic acid anhydrides. A further task of the invention is to provide improved processes for manufacturing herbicidal imidazolinones, like imazamox.

It has been found that 5-methyl-pyridine-2,3-dicarboxylic acid esters can be readily nitrosylated and further converted to the respective 5-formyl-pyridine-2,3-dicarboxylic acid esters. These compounds can be reduced to the respective alcohols and converted to 5-chloromethyl-pyridine-2,3-dicarboxylic acid anhydrides. The nitrosation of methyl-pyridines with strong bases such as butyl lithium at low temperatures is disclosed in Heterocycles 24 (1992) 1605, however, yields are very low for 3-methyl-pyridines.

Accordingly, in one aspect of the invention there is provided a process for manufacturing a 5-formyl-pyridine-2,3-dicarboxylic acid ester (I)

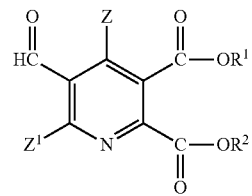

wherein
Z is hydrogen or halogen;
$Z^1$ is hydrogen, halogen, cyano or nitro and
$R^1$, $R^2$ are independently $C_1$-$C_{10}$-alkyl,
comprising the steps of
(i) reacting a compound of formula (II),

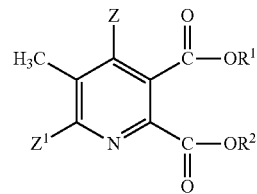

wherein the symbols are as in formula (I), with a nitrosation agent (III),

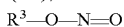

$$R^3—O—N=O \quad (III)$$

wherein $R^3$ is $C_1$-$C_8$-alkyl,
in the presence of an alkali metal or alkaline earth metal alcoholate in a polar aprotic solvent at a temperature of from −45 to 40° C., to obtain an oxime compound (IV),

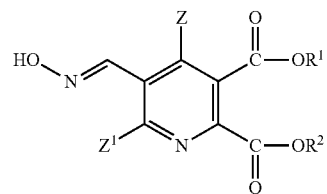

where Z, $Z^1$, $R^1$ and $R^2$ are as in formula (I), and
(ii) reacting oxime compound (IV) with an aliphatic $C_1$-$C_{10}$-aldehyde in the presence of an acid at a temperature in the range of from 0 to 100° C.

In a further aspect of the invention there is provided an oxime compound (IV) and the use thereof as an intermediate in the synthesis of herbicidal imidazolinones.

In yet a further aspect of the invention there is provided a method for manufacturing a 5-chloromethyl-pyridine-2,3-dicarboxylic acid anhydride (V)

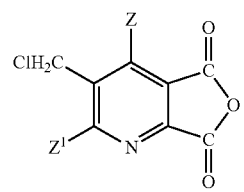

wherein

Z is hydrogen or halogen;

$Z^1$ is hydrogen, halogen, cyano or nitro;

comprising the steps of (i)/(ii) preparing a compound of formula (I) as described above, (iii) reducing compound (I) with a complex metal hydride in an diluting agent at a temperature in the range of from −20 to 60° C. and hydrolyzing the ester groups of compound (I) to obtain hydroxyl compound (VI),

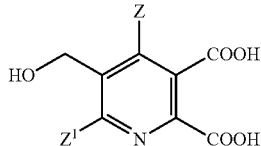

(VI)

where Z, $Z^1$ are as in formula (V), and (iv) treating hydroxyl compound (VI) with an chloride or oxychloride of phosphorus or sulfur to form anhydride (V).

Hydroxy compound (VI) is new, and this compound and its use as an intermediate for the synthesis of herbicidal imidazolinones are further provided by the invention.

In another aspect of the invention there is provided a process for preparing a herbicidal imidazolinone compound of formula (VII),

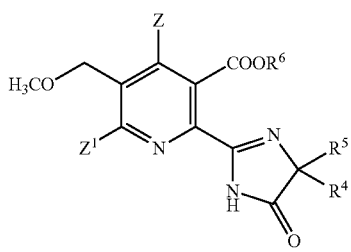

(VII)

wherein

Z, $Z^1$ are as defined in formula (I);

$R^4$ is $C_1$-$C_4$ alkyl;

$R^5$ is $C_1$-$C_4$ alkyl, $C_3$-$C_6$ cycloalkyl or $R^4$ and $R^5$, when taken together with the atom to which they are attached, represent a $C_3$-$C_6$ cycloalkyl group optionally substituted with methyl, and $R^6$ is hydrogen or a cation preferably selected from the group consisting of alkali metals, alkaline earth metals, manganese, copper, iron, zinc, cobalt, lead, silver, nickel, ammonium and organic ammonium.

The process of the invention yields compounds (I) in excellent yields and high purity, and thus is advantageous for producing 5-chloromethyl-pyridine-2,3-dicarboxylic acid anhydrides which are valuable intermediates in the synthesis of herbicidal imidazolinoes.

The starting materials, 3-methyl-pyridine-2,3-dicarboxylic esters (II) and their preparation are known e.g. from EP-A 0 933 362.

Preferred compounds of formula (II) are those where $Z=Z^1=H$ and $R^1$, $R^2$ are independently ($C_1$-$C_4$)-alkyl. Particularly preferred are compounds (II), where $Z=Z^1=H$ and $R^1$, $R^2$ are independently $CH_3$ and $C_2H_5$.

Alkyl nitrites, $R^3$—ONO with R being a linear or branched $C_1$-$C_8$-alkyl group, are suitable nitrosation agents. Preferred are Me-ONO, iso-Pe-ONO (3-methyl-1-butyl nitrite, iso-amyl nitrite), n-Bu-ONO and t-BuONO, with n-Bu-ONO being particularly preferred. Generally 0.9 to 2 equivalents of nitrosation agent are employed (based on compound (II)), preferred are 1.1 to 1.3 equivalents.

Bases suitable for use in the inventive process are alkali metal and earth alkaline metal alcoholates.

Preferred are alkali metal and earth alkaline metal $C_1$-$C_9$-alohalates, such as $NaOCH_3$, $NaOC_2H_5$, $KOCH_3$, $KOC_2H_5$, KO-tert-$C_4H_9$, $Ca(OCH_3)_2$, more preferred are $NaOCH_3$, $NaOC_2H_5$, $KOCH_3$ and $KOC_2H_5$. $NaOCH_3$ and $KOCH_3$ are particularly preferred. Mixtures of these bases can also be employed.

Typically 1 to 3, preferably 1 to 2, in particular 1 to 1,3 equivalents of base (based on compound (II)) are employed.

The reaction is generally carried out in a dipolar aprotic solvent. Preferred classes of solvents are sulfoxides, like dimethylsulfoxide (DMSO), cyclic sulfones, like sulfolane, N,N-dialkylamides, like N,N-dimethylformamide (DMF), N,N-dimethylacetamide (DMA), pyrrolidones, like N-methylpyrrolidone (NMP), cyclic ureas, like N,N-dimethylethylene urea (DMEU), and N,N-1,3,4-trimethylethylen-urea (TMEU). DMF, NMP and DMEU are particularly preferred. It is also possible to use a mixture comprising two or more of these solvents. The amount of solvent may vary to a large extent. Preferably 1 to 5 l, more preferably 1.5 to 3 l of solvent per mol of compound (II) are employed.

The reaction is carried out at a temperature in the range of from −45 to 40° C., preferably of from −10 to 30° C., in particular of from 0 to 25° C.

In a preferred embodiment compound (II) and the nitrosation agent are dissolved in the solvent, the mixture is cooled to the reaction temperature, base is added continuously or batchwise, and the reaction is stirred at the reaction temperature until completion.

Working up can be effected by conventional methods known to those skilled in the art, e.g. by adding aqueous acid, extraction of the product with water immiscible organic solvent and optional further purification of compound (IV) of the removal of the solvent.

In a preferred embodiment of the invention oxime (IV) is not isolated and the reaction mixture is directly used in step (ii) for a one-pot synthesis of compound (I).

Oxime compounds (IV) are novel and are valuable intermediates in organic synthesis, in particular in the synthesis of herbicidal imidazolinones, such as imazamox.

Preferred are compounds of formula (IV) where the symbols have the following meanings Z is preferably H.

$Z^1$ is preferably H.

$R^1$, $R^2$ are independently, preferably $C_1$-$C_8$-alkyl, in particular $C_1$-$C_4$-alkyl.

Preferred compounds (IV) are those where all symbols have the preferred meanings.

In a particularly preferred embodiment $Z=Z^1=H$ and $R^1=R^2=CH_3$.

In a further particularly preferred embodiment $Z=Z^1=H$ and $R^1\neq R^2=C_1$-$C_4$-alkyl, in particular $CH_3$ and n-$C_4H_9$. Due to partial trans esterfication during the reaction mixed esters (e.g. dimethyl, dibutyl, methyl butyl) are typically obtained. Such mixed esters can be used for further transformations without separation.

In step (ii) the oxime compound (IV) is subjected to a transoximation reaction to obtain formyl compound (I), as shown for preferred compounds (Ia) and paraformaldehyde:

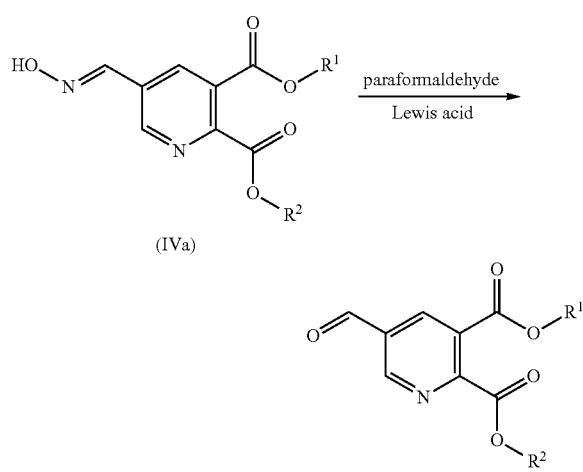

(IVa)

$R^1, R^2$=Me, Bu

In principle any aliphatic aldehyde can be used for the reaction, with linear or branched $C_1$-$C_8$-Aldehydes being preferred. Formaldehyde and acetaldehyde are especially preferred, in particular formaldehyde, e.g. as aqueous solution (formalin) or as paraformaldehyde.

Generally 1 to 20, preferably 5 to 10, more preferred 2 to 5 equivalents of aldehyde (based on compound (IV)) are employed.

A wide variety of acids, in particular Lewis acids, is useful for catalyzing the transoximation. Preferred are mineral acids, carboxylic acids, sulfonic acids, acidic ion ex-change resins, metal halides and metalloid halides, e.g. hydrochloric acid, hydrofluoric acid, hydrobromic acid, sulfuric acid, nitric acid, formic acid, acetic acid, propionic acid, oxalic acid, toluene sulfonic acid, benzene sulfonic acid, camphene sulfonic acid, citric acid, trifluoro acetic acid, $BF_3$, $AlCl_3$, $FeCl_2$, $SnCl_4$, $TiCl_4$ and $ZnCl_2$. Hydrochloric acid and sulfuric acid are particularly preferred, and are generally employed as aqueous solutions.

Typically 3 to 20, preferably 3 to 5, equivalents of acid are used based on compound (IV).

The reaction is generally carried out in an aqueous medium which may comprise further dipolar aprotic or protic solvents, in particular the solvents used in step (i).

The reaction is generally carried out at a temperature in the range of from 0 to 100° C., preferably 20 to 80° C., more preferably 30 to 65° C.

In a preferred embodiment compound (IV) and the aldehyde diluted in an aqueous acid medium and stirred until the reaction is completed.

Working up can be effected by conventional methods known in the art, e.g. the product (compound (I)) can be extracted with a water immiscible organic solvent, dried and optionally further purified after removal of the solvent.

In another preferred embodiment steps (i) and (ii) are carried out as a one-pot reaction. In this embodiment aldehyde and aqueous acid are added to the reaction mixture obtained in step (i), the mixture is brought to the desired reaction temperature for step (ii) and stirred until formation of the desired product (I) is completed.

Working up can be conducted in the manner described above. Further purification of formyl compound (I) is possible with conventional methods, such as chromatographic methods or recrystallization. Typically, the crude product is directly used as an inter-mediate in the further synthesis of herbicidal imidazolinones (VII).

In one embodiment of the invention formyl compound (I) is reduced with a complex metal hydride to afford hydroxyl-compound (VI) as exemplified by preferred compounds (Ia) and (VIa):

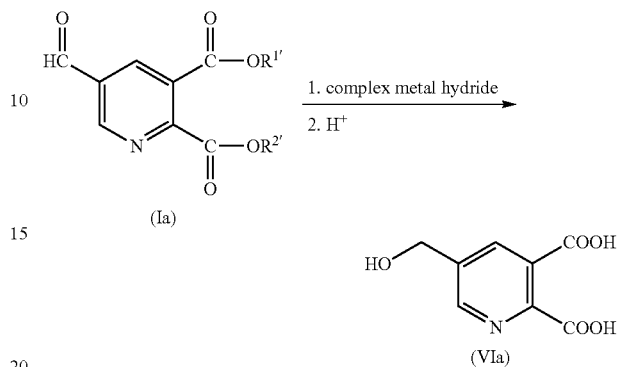

$R^{1'}, R^{2'}$=Me, Bu

Typical complex metal hydrides include compounds $M^1_x$ $(M^2H_y)$ where $M^1$ is an alkali metal, preferably Li or Na or K, $M^2$ is a metal or metalloid, preferably B or Al, and x and y depend on the oxidation state of the metal. Preferred are $LiBH_4$, $NaBH_4$, $KBH_4$, Li—$AlH_4$, $NaAlH_4$ and $KAlH_4$. Preferred are compounds that are relatively stable towards water and alcohols, such as $NaBH_4$ and $KBH_4$. A technical solution of $NaBH_4$ in soda lye (e.g. Borol® available from Rohm and Haas, Philadelphia, USA, or Sigma Aldrich, Saint Louis, USA) is particularly preferred.

Generally 1 to 3, preferably 1 to 1.5 equivalents (based on active hydrogen) of complex metal hydride are employed per equivalent of compound (I).

The reducing agent may be used as a solid or as a solution or suspension in a suitable solvent. Such solvents are known to those skilled in the art and include, e.g. water, primary, secondary and tertiary alcohols, preferably having from 1 to 6 carbon atoms, such as isopropanol, ethanol and methanol. Preferably such solutions or suspensions are stabilized with alkali.

Employing the reducing agent as an aqueous solution or suspension is preferred. In preferred embodiments metal salts, such as LiCl or $NaHSO_4$ are added to the solution.

The reduction is generally carried out at a temperature in the range of from −20 to 60° C., preferably −10 to 40° C., in particular −5 to 25° C.

In a preferred embodiment formyl compound (I) is added to a solution/suspension of the reducing agent and the reaction mixture is stirred at the desired temperature up to the desired degree of conversion.

Working up can be achieved by conventional methods known to those skilled in the art. In order to obtain the free acid the pH value is adjusted by addition of a strong acid, such as HCl. The raw product can be isolated, e.g. by removal of the solvent and optional drying. Further purification can be effected e.g. by recrystallization or chromatographic methods. In a preferred embodiment, the raw product is not further purified, but is directly used in the following production step, (iv) simultaneous chlorination and formation of the anhydride, as exemplified with preferred compounds (VIa) and (Va):

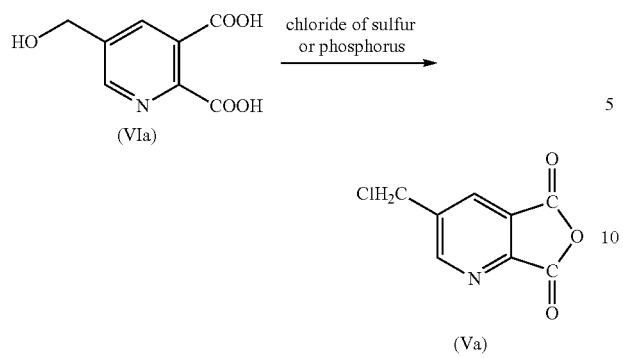

In step (iv) chlorides and oxychlorides of sulfur and phosphorus are employed as combined chlorinating and dehydrating agents, such as SOCl$_2$, SO$_2$Cl$_2$, PCl$_3$, PCl$_5$, POCl$_3$. Preferred are SOCl$_2$ and POCl$_3$ with SOCl$_2$ being particularly preferred.

Typically 1 to 10, preferably 2 to 5, in particular 2 to 4 equivalents of chlorinating/dehydrating agent are used. Excess chlorinating agent may be recovered after completion of the reaction.

Either the chlorinating/dehydrating agent is used as a solvent or a further inert solvent is added. Suitable solvents include aromatic hydrocarbons and ethers, such as toluene, xylenes, mesitylene, chlorobenzenes, dichloromethane, 1,2-dichloroethane, diethyl ether, cyclolpentyl methyl ether, methyl tert.-butyl ether (MTBE), tetrahydrofurane (THF) and dioxane, with toluene being preferred.

The reaction is typically carried out under reflux, i.e. at the boiling point of the solvent or chlorinating agent.

In a preferred embodiment hydroxyl compound (VI) is taken up in a solvent, heated to reflux, followed by addition of the chlorinating agent and maintaining under reflux until completion of the reaction.

Working up can be achieved by conventional methods known to those skilled in the art, such as removal of the solvent and drying by azeotropic distillation, e.g. with toluene.

If desired the product (V) may be further purified, however, the product thus obtained is sufficiently pure for further conversion to herbicidal imidazolinones (VII).

The compounds of formula (V) are valuable intermediates in organic synthesis. They are especially useful for conversion to herbicidal imidazolinone compounds (VII).

In one aspect of the invention there is provided a process for producing a herbicidal imidazolinone of formula (VII) comprising the steps of:
(i)/(ii)/(iii)/(iv) preparing a compound of formula (V) as described above,
(v-a) reacting compound (V) with an 2-aminoalkane carboxamide (VIII)

where R$^4$ and R$^5$ are as in formula (VII),
or
(v-b) reacting compound (V) with a 2-aminoalkane carbonitrile (IX) (v-b1),

where R$^4$ and R$^5$ are as in formula (VII), and (v-b2) hydrolyzing the nitrile group to yield the amide (X), where
Z, Z$^1$, R$^4$, R$^5$, R$^6$ are as defined in formula (VII);
(vi) reacting compound (X) with CH$_3$OM or MOH/CH$_3$OH (where M is an alkali metal cation, preferably Na or K) followed by acidification to form the herbicidal imidazolinone (VII).

In one embodiment step (v-a) can be carried out in analogy to the procedure disclosed in example 10 of EP-A 0 322 616. Compound (V), a substituted 2-aminoalkane carboxamide (VIII) and a tertiary amine, preferably triethylamine are reacted in a polar aprotic solvent, such as acetonitrile, to yield an ammonium salt (VII), which can be acidified to an acid (VII).

In another preferred embodiment compound (V) is reacted with an 2-aminoalkane carbonitrile (IX) (step v-b1) to form a 2-carbamoyl-nicotinic acid (XI)

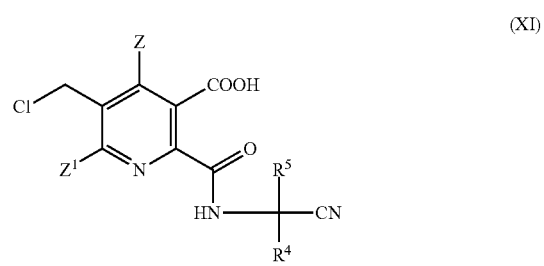

where R$^4$ and R$^5$ are defined as in formula (VII) which is further hydrolyzed (step (v-b2)) to yield the amido compound (X).

In a preferred embodiment, compound (Va) is reacted with preferred 1-aminoalkane carbonitrile (IXa) to form preferred carbonitrile compound (XIa):

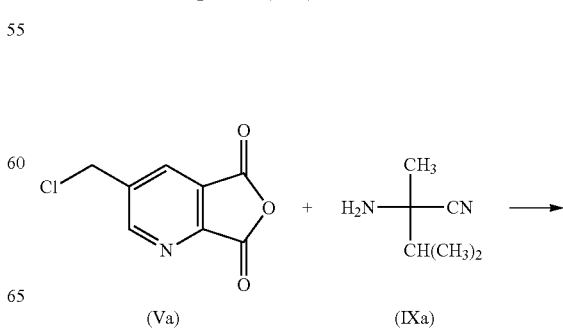

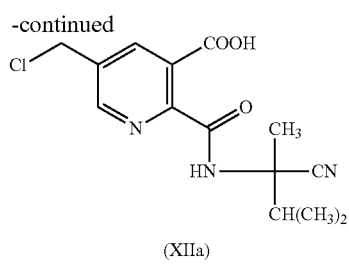

(XIIa)

Aminonitriles (IX) are commercially available or can be prepared by methods known in the art. Generally 0.8 to 1.2 equivalents aminonitrile (IX) per equivalent of compound (V) are used, preferably 0.95 to 1.1.

The reaction is carried out in a solvent which is preferably selected from aromatic hydrocarbons, preferably toluene, mesitylenes, chlorinated aromatic hydrocarbons, such as chlorobenzene, dichlorobenzene, chlorinated hydrocarbons, such as 1,2-dichloro-ethane, dichloromethane, acetic acid, and mixtures thereof.

If acetic acid is not used as the main solvent, addition of 0.5 to 4 equivalents, preferably 1 to 3 equivalents (based on compound (V)), is advantageous. Further advantageous additives that improve the selectivity of the ring-opening reaction (2 versus 3 position) are listed in U.S. Pat. No. 4,562,257, and comprise pyridine, 4-picoline, 2-picoline and quinoline.

The reaction is generally carried out at a temperature range of from about 40 to about 120° C., preferably of from about 60 to about 100° C. The reaction time is generally from about 1 to about 3 h.

In a preferred embodiment compound (V) is dissolved in the solvent and brought to the reaction temperature, and aminonitrile (IX) is gradually added. After completion of the reaction and cooling, nitrile compound (XI) can be isolated by standard methods.

In a preferred embodiment, however, compound (XI) is not isolated but the reaction mixture is directly used in the following hydrolyzation step of the nitrile, e.g.

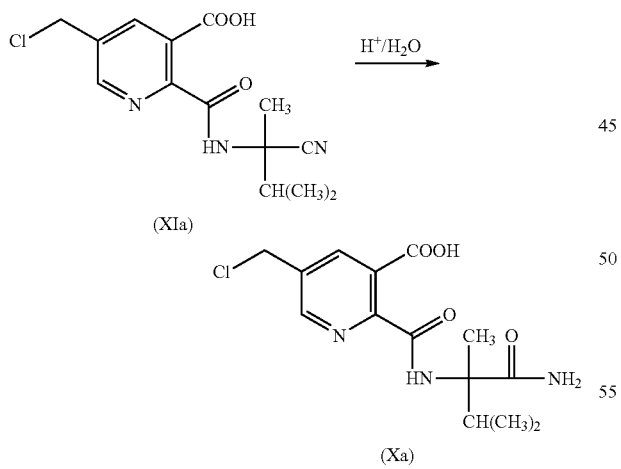

In a typical procedure a slight excess (e.g. 1.1 to 1.5 equivalents based on (XI)) of a strong mineral acid, preferably sulfuric acid (preferably in a concentration of 30 to 98%) and water (e.g. 2 to 10 equivalents) are added at a temperature which is generally in the range of about 30 to 120° C., preferably 50 to 90° C. The mixture is further stirred until complete conversion. The reaction time is generally from 1 to 8 h, preferably 1 to 5 h.

Working up and isolation can be achieved by standard methods, such as precipitation from an aqueous solution (e.g. as its ammonium salt). In a preferred embodiment the reaction mixture is directly used in the following reaction step.

In a further step (vi) of the inventive process a herbicidal imidazolinone compound (VII) is prepared by conversion of amido compound (X).

In one alternative of step (vi) amido compound (X), preferably in the form of an ammonium salt ($R^6$ is $HNR_3$), is reacted with an alkali metal methoxide, preferably $NaOCH_3$ in methanol in analogy to example 11 of EP 0 322 616. The resulting suspension is held at reflux until complete conversion. After cooling the mixture is acidified to obtain compound (III) either as the ammonium salt (acidification to a pH of about 4) or the free acid (acidification to pH ≤2).

In a further preferred embodiment, compound (X), preferably the reaction mixture from step (v), is reacted with methanol (generally 2 to 100 equivalents based on (X)) in the presence of an aqueous base (generally 3 to 100 equivalents based on (X)), the base being preferably selected from MOH and $MOCH_3$, where M is an alkali metal cation, preferably Na or K, particularly Na.

The reaction is carried out at a temperature in the range of from 20 to 120° C., preferably 40 to 90° C. The reaction can be carried out at atmospheric pressure or at elevated pressure, preferably the pressure forming at the desired reaction temperature. The reaction time is generally from 1 to 8 h, preferably from 1 to 5 h.

Isolation of product (VII) can be achieved by standard methods. In a preferred embodiment water is added and organic solvents are distilled off. The residue can be taken up in water and acidified, whereupon compound (VII) precipitates. After filtration the crude product can be further purified, e.g. by stirring with water or recrystallization.

In a further embodiment of the invention there is provided a process for preparing herbicidal imidazolinones of formula (VII) comprising the steps of (i)/(ii)/(iii)/(iv)/(v-b1) preparing a carbonitrile (XI) as described above and (v-b2)/(vi) reacting compound (XI) with a base selected from MOH and $MOCH_3$, where M is an alkali metal cation, and (aqueous) $H_2O_2$ in methanol, optionally followed by acidification

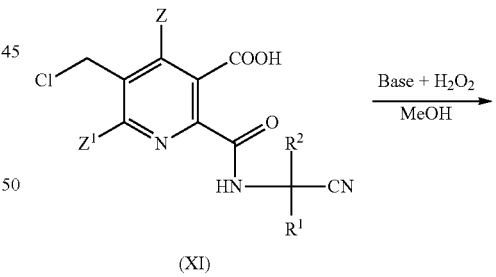

(XI)

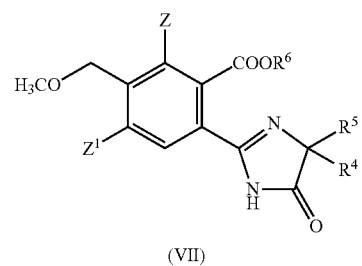

(VII)

The reaction can be carried out in analogy to the procedures described in EP-A 0 144 595.

In a further embodiment of the invention there is provided a process for preparing a compound of formula (XII)

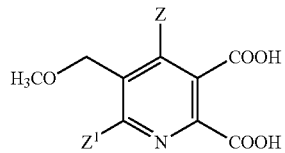
(XII)

where Z, Z$^1$ are as in formula (I), comprising the steps of (i)/(ii)/(iii)/(iv) preparing a compound of formula (V) as described above, and (v-α) reacting compound (V) methanol in the presence of MOH or MOCH$_3$, where M is an alkali metal cation, followed by acidification.

In a preferred embodiment (V) is dissolved in methanol (generally 2 to 100 equivalents based on (V)), and base is added (generally 3 to 100 equivalents). In a preferred embodiment water is added, preferably 5 to 200% by weight based on the base. The base is preferably selected from NaOH, KOH, NaOCH$_3$ and KOCH$_3$, NaOH, particularly as a 50% by weight aqueous solution, is especially preferred.

The reaction temperature is generally in the range of from about 20 to about 120° C., preferably about 40 to about 90° C. The reaction is generally carried out at ambient pressure or elevated pressure. The reaction time is generally from 1 to 8 h, preferably from 1 to 5 h.

Working up and isolation of compound (XII) can be achieved by standard measures. Compound (XII) can be treated with a dehydrating agent, such as acetic anhydride, to form the anhydride (XIII),

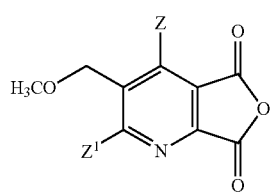
(XIII)

Anhydride (XIII) can be converted to herbicidal imidazolinones (VII) in analogy to the conversion of compound (V). Preparation of compounds (VII) by a respective process is a further object of the invention.

According to this embodiment of the invention a process is provided for preparing a herbicidal imidazolinone compound of formula (VII), above comprising the steps of:

(i)/(ii)/(iii)/(iv) preparing a compound of formula (V) as described above, (v-α) reacting compound (V) in methanol with MOH or MOCH$_3$, where M is an alkali metal cation, followed by acidification, to form compound (XII)

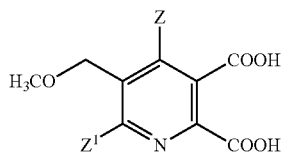
(XII)

where Z, Z$^1$ are as in formula (I), and (v-β) treating compound (XII) with a dehydrating agent to form anhydride (XIII),

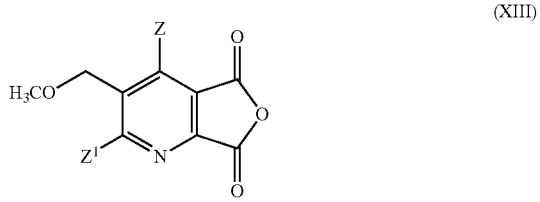
(XIII)

where Z, Z$^1$ are as in formula (II), and either (v-γa1) reacting anhydride (XIII) with aminonitrile (IX),

$H_2N—CR^4R^5—CN$ (IX)

where R$^4$ and R$^5$ are as in formula (VII), to obtain nitrile compound (XIV),

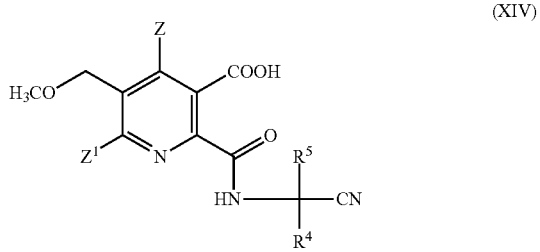
(XIV)

where the symbols are as in formula (VII), (v-γa2) hydrolyzing the nitrile group in compound (XIV) to obtain amide (XV),

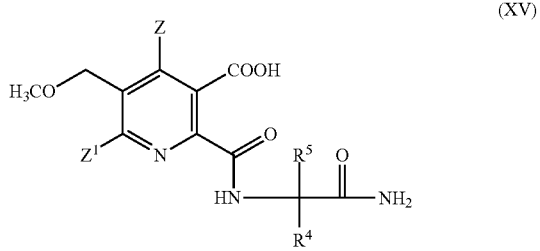
(XV)

where the symbols are as in formula (VII), or (v-γb) reacting anhydride (XIII) with an amino carboxamide (VIII)

$H_2N—CR^4R^5—CONH_2$ (VIII)

where R$^4$ and R$^5$ are as in formula (VII), to obtain amide (XV), and (vi-α) condensation of amide (XV) to yield a herbicidal imidazolinone (VII).

The invention is illustrated by the following examples without limiting it thereby.

EXAMPLES

Example 1

5-(Hydroxyiminomethyl)-pyridine-2,3-dicarboxylic acid butyl/methyl ester (Mixture)

50 g (0.24 mol) MPDC-DME (5-methyl-pyridine-2,3-dicarboxylic acid dimethyl ester (IIa)) were mixed at −45° C. with 27.1 g (0.26 mol) n-BuONO in 750 ml DMF. Afterwards 25.1 g (0.36 mol) KOMe were added in portions at the same temperature, the mixture was stirred for 2 h at the same temperature, and subsequently added to a mixture of ice water (2500 ml) and concentrated HCl (250 ml). The resulting mixture was extracted three times with 200 ml methyl tert.-butyl ether (MTBE), the combined organic phases were washed once with water and once with saturated brine, dried over magnesium sulphate, and the organic solvent was subsequently removed in vacuo.

41.7 g of an about 1:1 mixture of 5-(hydroxyiminomethyl)-pyridine-2,3-dicarboxylic acid butyl ester/methyl ester were obtained, having a 90% purity ($^1$H-NMR). Yield: 67%.

$^1$H-NMR (CDCl$_3$): 0.95 ppm (m, 6H, CH$_3$), 1.45 ppm (m, 4H, CH$_2$), 1.75 ppm (m, 4H, CH$_2$), 3.95 ppm (s, 2H, OCH$_3$), 4.0 ppm (m, 2H, OCH$_2$), 4.05 ppm (s, 2H, OCH$_3$), 4.4 ppm (m, 2H, OCH$_2$), 8.2 ppm (s, 2H, 2× CH), 8.35 ppm (s, 2H, 2× CH), 8.95 ppm (s, 2H, 2× CH=N).

Example 2

5-(Hydroxyiminomethyl)-pyridine-2,3-dicarboxylic acid butyl ester/methyl ester (Mixture)

20 g (0.1 mol) MPDC-DME were mixed at −10° C. with 10.8 g (0.11 mol) n-BuONO in 30 ml DMF. Afterwards 7.7 g (0.14 mol) NaOMe were added in portions at the same temperature, the mixture was stirred for 0.5 h at the same temperature, and subsequently added to a mixture of ice water (1000 ml) and concentrated HCl (100 ml). The resulting mixture was extracted three times with 100 ml MTBE, the combined organic phases were washed once with water and once with saturated brine, dried over magnesium sulphate, and the organic solvent was subsequently removed in vacuo.

18.1 g of an about 1:1 mixture of 5-(hydroxyiminomethyl)-pyridine-2,3-dicarboxylic acid butyl ester/methyl ester were obtained, having a 90% purity ($^1$H-NMR). Yield: 72%.

Example 3

5-(Hydroxyiminomethyl)-pyridine-2,3-dicarboxylic acid butyl ester/methyl ester (Mixture)

20 g (0.1 mol) MPDC-DME were mixed at 0° C. with 10.8 g (0.11 mol) n-BuONO in 30 ml DMF. Afterwards 7.7 g (0.14 mol) NaOMe were added in portions at the same temperature, the mixture was stirred for 0.5 h at the same temperature, and subsequently added to a mixture of ice water (1000 ml) and concentrated HCl (100 ml). The resulting mixture was extracted three times with 100 ml MTBE, the combined organic phases were washed once with water and once with saturated brine, dried over magnesium sulphate, and the organic solvent was subsequently removed in vacuo.

19.5 g of an about 1:1 mixture of 5-(hydroxyiminomethyl)-pyridine-2,3-dicarboxylic acid butyl ester/methyl ester were obtained, having a 90% purity ($^1$H-NMR). Yield: 78%.

Example 4

5-(Hydroxyiminomethyl)-pyridine-2,3-dicarboxylic acid butyl ester/methyl ester (Mixture)

20 g (0.1 mol) MPDC-DME were mixed at 20° C. with 10.8 g (0.11 mol) n-BuONO in 30 ml DMF. Afterwards 7.7 g (0.14 mol) NaOMe were added in portions at the same temperature, the mixture was stirred for 0.5 h at the same temperature, and subsequently added to a mixture of ice water (1000 ml) and concentrated HCl (100 ml). The resulting mixture was extracted three times with 100 ml MTBE, the combined organic phases were washed once with water and once with saturated brine, dried over magnesium sulphate, and the organic solvent was subsequently removed in vacuo.

16.0 g of an about 1:1 mixture of 5-(hydroxyiminomethyl)-pyridine-2,3-dicarboxylic acid butyl ester/methyl ester were obtained, having a 95% purity ($^1$H-NMR). Yield: 68%.

Example 5

5-Formyl-pyridine-2,3-dicarboxylic acid butyl ester/methyl ester (Mixture)

41.2 g (0.17 mol) of a 5-(hydroxyiminomethyl)-pyridine-2,3-dicarboxylic acid butyl ester/methyl ester mixture were stirred in 252 g 5 percent aqueous hydrochloric acid with 58.2 g (1.9 mol) paraformaldehyde at 60° C. for 2 h. After cooling the mixture was extracted three times with 100 ml dichloromethane, the combined organic phases were washed once with water and once with saturated brine, dried over magnesium sulphate, and the organic solvent was subsequently removed in vacuo.

36.6 g of a 90 percent mixture (about 1:1) of 5-formyl-pyridine-2,3-dicarboxylic acid butyl ester/methyl ester were obtained. Yield: 86%.

$^1$H-NMR (CDCl$_3$): 0.95 ppm (m, 6H, CH$_3$), 1.45 ppm (m, 4H, CH$_2$), 1.75 ppm (m, 4H, CH$_2$), 4.0 ppm (s, 2H, OCH$_3$), 4.05 ppm (s, 2H, OCH$_3$), 4.4 ppm (m, 2H, OCH$_2$), 4.45 ppm (m, 2H, OCH$_2$), 8.7 ppm (s, 2H, 2× CH), 9.25 ppm (s, 2H, 2× CH), 10.2 ppm (s, 2H, 2× CHO).

Example 6

5-Formyl-pyridine-2,3-dicarboxylic acid butyl ester/methyl ester (Mixture) (One-Pot-Procedure)

20 g (0.1 mol) MPDC-DME were mixed at 0° C. with 10.8 g (0.11 mol) n-BuONO in 30 ml DMF. Afterwards 7.7 g (0.14 mol) NaOMe were added in portions at the same temperature, the mixture was stirred for 0.5 h at the same temperature, and subsequently stirred at 0° C. to 244 g 5 percent aqueous HCl. 31.6 g (1.5 mol) paraformaldehyde were added, and the mixture was stirred at 60° C. for 2 h. After cooling the mixture was extracted three times with 100 ml dichloromethane, the combined organic phases were washed once with water and once with saturated brine, dried over magnesium sulphate, and the organic solvent was subsequently removed in vacuo.

16.6 g of a 82 percent mixture (about 1:1) of 5-formyl-pyridine-2,3-dicarboxylic acid butyl ester/methyl ester were obtained. Yield: 64%.

Example 7

5-Hydroxymethyl-pyridine-2,3-dicarboxylic acid 10 g (0.04 mol) of a 90 percent 5-formyl-pyridine-2,3-dicarboxylic acid butyl ester/methyl ester mixture were added at 0° C. to a solution of technical grade sodium borohydride (Sigma-Aldrich) in 100 ml water, and stirred for 1 h at this temperature. Afterwards the pH-value was adjusted to 2 with 2N HCl under cooling, the water was evaporated in vacuo, and the residue was twice dried aceotropically with 100 ml toluene. The isolated product still contains salt and is 30 percent according to $^1$H-/$^{13}$C-NMR. Yield: 85%.

$^1$H-NMR (DMSO-$d_6$): 4.65 ppm (s, 2H, CH$_2$), 6.6 ppm (s, 1H, OH), 8.35 ppm (s, 1H, CH), 8.75 ppm (s, 1H, CH).

Example 8

5-Chloromethyl-pyridine-2,3-dicarboxylic acid anhydride (3-chloromethyl-furo[3,4-b]pyridine-5,7-dione) (Va)

5 g (0.008 mol) 5-hydroxymethyl-pyridine-2,3-dicarboxylic acid (30 percent) were dissolved in 20 ml toluene and heated to reflux. Subsequently 9.1 g (0.08 mol) thionylchloride were added. After 3 h at reflux the reaction mixture was evaporated to dryness in vacuo, the residue was twice dried aceotropically with 40 ml toluene, taken up in 40 ml hot toluene, and the toluene was distilled off in vacuo.

0.8 g 5-chloromethyl-pyridine-2,3-dicarboxylic acid anhydride were obtained in a purity of 90% ($^1$H-NMR). Yield: 48%.

$^1$H-NMR (CDCl$_3$): 4.8 ppm (s, 2H, CH$_2$), 8.45 ppm (s, 1H, CH) 9.2 ppm (s, 1H, CH).

Example 9

Synthesis of Imazamox (VIIa)

(a) Synthesis of Carbonitrile (XIa)

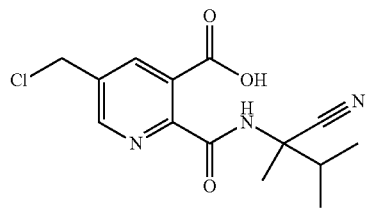 [SMILES: CC(C)C(C)(C#N)NC(=O)c1ncc(CCl)cc1C(=O)O]

9.6 g (48 mmol) anhydride (Va), 40.0 g (435 mmol) toluene and 6.7 g (112 mmol) ace-tic acid were charged to a reactor and heated up to 69° C. 7.2 g (51 mmol) α-amino-1,2-dimethyl butyronitrile (Va) were added over 25 min at a temperature between 72° C. and 76° C. The mixture was stirred for additional 90 min at 75° C. After cooling the mixture was directly used in the next stage.

(b) Synthesis of 2-[(1-carbamoyl-1,2-dimethylpropyl)carbamoyl]-5-chloromethyl nicotinic acid (Xa)

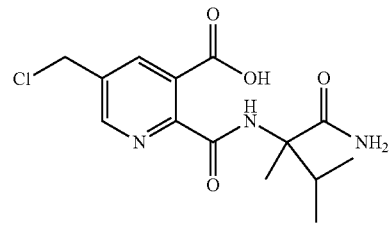 [SMILES: CC(C)C(C)(NC(=O)c1ncc(CCl)cc1C(=O)O)C(N)=O]

To 14.9 g (48 mmol) nitrile (XI) (from stage (a)), 6.0 g (59 mmol) sulfuric acid (98%) was added at 69° C. to 80° C. within 5 min. 4.1 g (228 mmol) water was added at 70° C. to 78° C. and stirring continued at 69° C. for 5 h. The emerging product forms a toluene insoluble oil. The reaction mixture was used without working up in the following stage.

(c) Synthesis of Imazamox (VIIa)

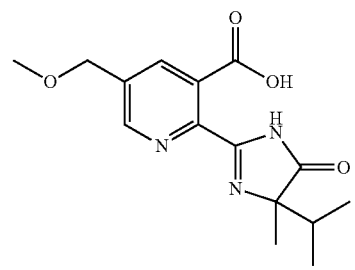 [SMILES: COCc1cnc(C2=NC(C)(C(C)C)C(=O)N2)c(C(=O)O)c1]

To 15.7 g (48 mmol) amido compound (Xa) (reaction mixture from stage (b)) 94 g (2.94 mol) methanol was added at 65° C. and subsequently 42 g (525 mmol) NaOH (50% in water). The solution turned into a suspension, and stirring was continued for additional 90 min.

80 g water was added and solvents were removed at 50° C. and 80-8 mbar. Residue was dissolved in water and the basic solution acidified with 29 g sulfuric acid (98%). Imazamox precipitated from pH 4 on. The suspension was filtered at room temperature and washed with 100 ml water.

Yield: 16.5 g (82% pure, 44 mmol, 92%)

Purity was enhanced to >95% (HPLC) by stirring the crude product with water.

Example 10

Synthesis of 5-methoxymethyl-pyridine-2,3-dicarboxylic acid (XIIa)

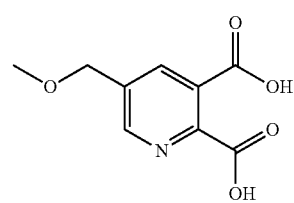

(XIIa)

7.0 g (35 mmol) 5-chloromethyl-pyridine-2,3-dicarboxylic acid anhydride (Va) were dissolved in 165 g (5.16 mol)

methanol at room temperature, causing formation of monoesters. 14 g (350 mmol) NaOH (50% in water) were slowly added whereupon the temperature rose to 50° C. and carboxylate started to precipitate. Stirring was continued for additional 5 h at 65° C.

The solvents were then removed in vacuo, and the solid residue was dissolved in 53 g water and acidified with 19 g sulfuric acid (98%) up to pH=1.5. The aqueous solution was extracted three times with 90 g THF at 40° C. and the combined organic phases were concentrated to dryness.

Yield: 7.4 g (32 mmol, 90%)

The invention claimed is:

1. A process for manufacturing a compound of formula (I)

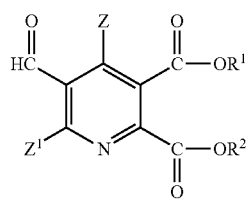
(I)

wherein
Z is hydrogen or halogen;
$Z^1$ is hydrogen, halogen, cyano or nitro and
$R^1$, $R^2$ are independently $C_1$-$C_{10}$-alkyl,
comprising
(i) reacting a compound of formula (II),

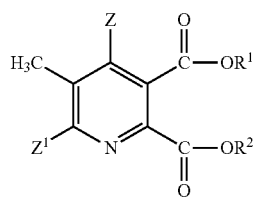
(II)

with a compound of formula (III)

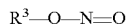
(III)

wherein $R^3$ is $C_1$-$C_8$-alkyl,
in the presence of an alkali metal or alkaline earth metal alcoholates or carbonates in a polar aprotic solvent at a temperature of from −45 to 40° C., to obtain a compound of formula (IV)

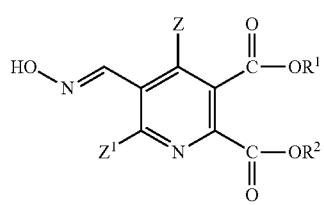
(IV)

and
(ii) reacting the compound of formula (IV) with an aliphatic $C_1$-$C_{10}$-aldehyde in the presence of an acid at a temperature in the range of from 0 to 100° C. to afford the compound of formula (I).

2. The process as claimed in claim 1, wherein steps (i) and (ii) are carried out as a one-pot reaction.
3. The process as claimed in claim 1, wherein $R^1$ and $R^2$ are $CH_3$ and/or $C_4H_9$.
4. The process as claimed in claim 1, wherein Z and $Z^1$ in formula (I), (II) and (IV) are H.
5. The process as claimed in claim 1, wherein the nitrosation agent in step (i) is n-butyl nitrite.
6. The process as claimed in claim 1, wherein the base in step (i) is $NaOCH_3$ or $KOCH_3$.
7. The process as claimed in claim 1, wherein the aliphatic aldehyde in step (ii) is para formaldehyde.
8. The process as claimed in claim 1, wherein the acid is selected from the group consisting of hydrochloric acid and sulfuric acid.
9. A process for manufacturing a compound of formula (V)

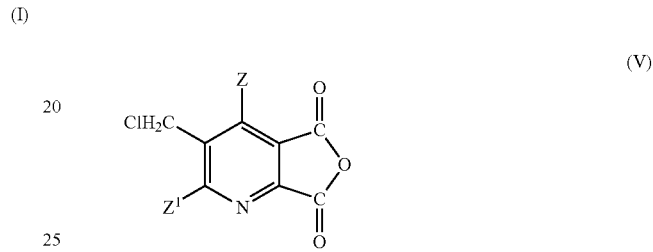
(V)

wherein
Z is hydrogen or halogen;
$Z^1$ is hydrogen, halogen, cyano or nitro;
comprising
(i)/(ii) preparing a compound of formula (I) according to the process of claim 1,
(iii) reducing the compound of formula (I) with a complex metal hydride in an diluting agent at a temperature in the range of from −20 to 60° C. and hydrolyzing the ester groups of the compound of formula (I) to obtain a compound of formula (VI)

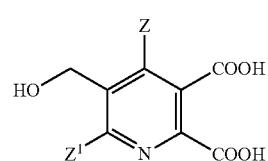
(VI)

and
(iv) treating the compound of formula (VI) with a chloride or oxychloride of phosphorus or sulfur to form the compound of formula (V).
10. A process for manufacturing a compound of formula (VII),

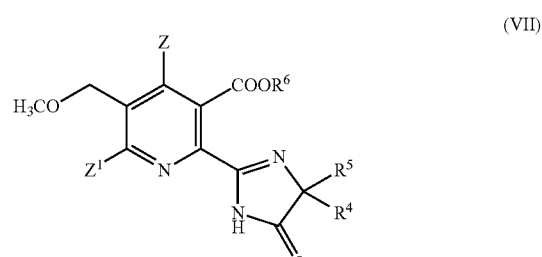
(VII)

wherein

Z is hydrogen or halogen;

$Z^1$ is hydrogen, halogen, cyano or nitro;

$R^4$ is $C_1$-$C_4$ alkyl;

$R^5$ is $C_1$-$C_4$ alkyl, $C_3$-$C_6$ cycloalkyl or $R^4$ and $R^5$; when taken together with the atom to which they are attached, represent a $C_3$-$C_6$ cycloalkyl group optionally substituted with methyl, and $R^6$ is hydrogen or a cation;

comprising (i)/(ii)/(iii)/(iv) preparing a compound of formula (V) according to the process of claim 9

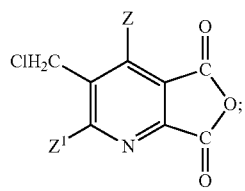
(V)

(v-a) reacting the compound of formula (V) with a compound of formula (VIII)

or (v-b) reacting the compound of formula (V) with a compound of formula (IX)

(v-b1),

$R^1$, $R^2$ are independently $C_1$-$C_{10}$-alkyl, and (v-b2) hydrolyzing the nitrile group to yield a compound of formula (X),

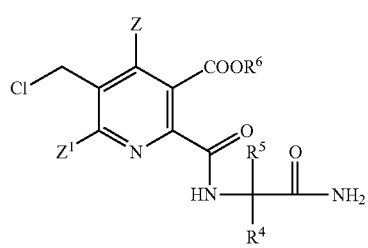
(X)

wherein (vi) reacting the compound of formula (X) with $CH_3OM$ or $MOH/CH_3OH$, wherein M is an alkali metal cation, preferably Na or K, followed by acidification to form the compound of formula (VII).

11. A process for manufacturing a compound of formula (VII) as disclosed in claim 10, comprising (i)/(ii)/(iii)/(iv) preparing the compound of formula (V) according to the process of claim 9

(v-b1) reacting the compound of formula (V) with a compound of formula (IX)

to form a compound of formula (XI)

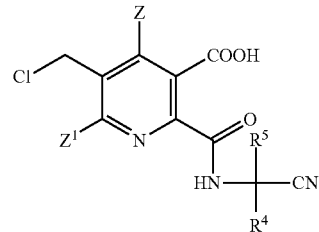
(XI)

(vi) reacting compound (XI) with a base selected from MOH and $MOCH_3$, where M is an alkali metal cation, and aqueous $H_2O_2$ in methanol, optionally followed by acidification to form the compound of formula (VII).

12. A process for manufacturing a herbicidal imidazolinone compound of formula (VII), as disclosed in claim 10, comprising (i)/(ii)/(iii)/(iv) preparing a compound of formula (V) according to the process of claim 9;

(v-α) reacting the compound of formula (V) in methanol with MOH or $MOCH_3$, where M is an alkali metal cation, followed by acidification, to form compound (XII);

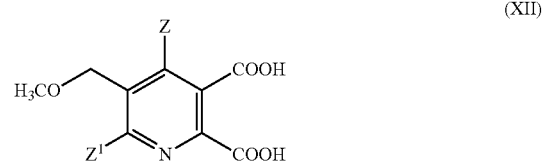
(XII)

wherein

Z is hydrogen or halogen;

$Z^1$ is hydrogen, halogen, cyano or nitro;

(v-β) treating the compound of formula (XII) with a dehydrating agent to form a compound of formula (XIII);

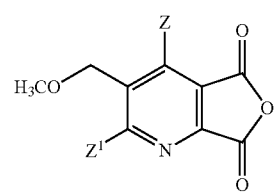
(XIII)

and either (v-γa1) reacting the compound for formula (XIII) with a compound of formula (IX),

to obtain a compound of formula (XIV),

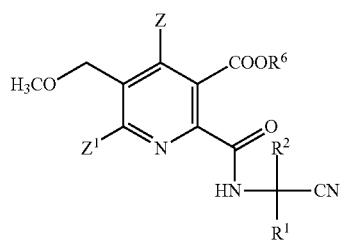 (XIV)

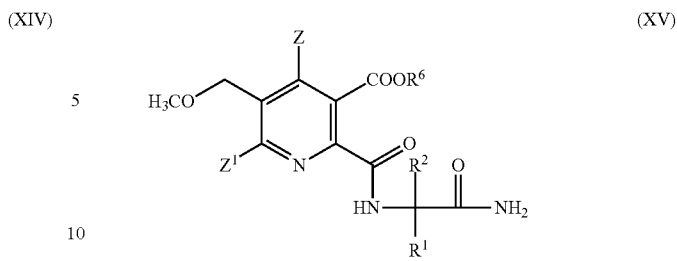 (XV)

wherein $R^1$ is $C_1$-$C_4$ alkyl;

$R^2$ is $C_1$-$C_4$ alkyl, $C_3$-$C_6$ cycloalkyl or $R^4$ and $R^5$; when taken together with the atom to which they are attached, represent a $C_3$-$C_6$ cycloalkyl group optionally substituted with methyl; and $R^6$ is hydrogen or a cation;

(v-γa2) hydrolyzing the nitrile group in the compound of formula (XIV) to obtain a compound of formula (XV), where the symbols are as in formula (VII), or (v-γb) reacting anhydride (XIII) with an amino carboxamide (VIII)

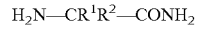 (VIII)

to obtain the compound of formula (XV), and (vi-α) condensation of the compound of formula (XV) to yield the compound of formula (VII).

\* \* \* \* \*